United States Patent [19]

Lee et al.

[11] Patent Number: 5,241,470
[45] Date of Patent: Aug. 31, 1993

[54] PREDICTION OF PROTEIN SIDE-CHAIN CONFORMATION BY PACKING OPTIMIZATION

[75] Inventors: Christopher Lee, Menlo Park; Subramanian Subbiah, Woodside, both of Calif.

[73] Assignee: The Board of Trustees of the Leland Stanford University, Stanford, Calif.

[21] Appl. No.: 823,790

[22] Filed: Jan. 21, 1992

[51] Int. Cl.⁵ ............................................. G06F 15/46
[52] U.S. Cl. .......................... 364/413.15; 364/413.13; 436/86
[58] Field of Search ...................... 364/413.15, 413.13; 436/86

[56] References Cited

U.S. PATENT DOCUMENTS

| | | | |
|---|---|---|---|
| 4,378,218 | 3/1983 | Fletterick et al. | 434/279 |
| 4,704,692 | 11/1987 | Ladner | 364/496 |
| 4,855,931 | 8/1989 | Saunders | 364/499 |
| 4,881,175 | 11/1989 | Ladner | 364/496 |
| 4,908,773 | 3/1990 | Pantoliano et al. | 364/496 |
| 4,946,778 | 8/1990 | Ladner et al. | 435/69.5 |
| 4,980,288 | 12/1990 | Bryan et al. | 435/222 |
| 5,025,388 | 6/1991 | Cramer, III et al. | 364/496 |

OTHER PUBLICATIONS

Jay W. Ponder et al., *Tertiary Templates for Proteins Use of Packing Criteria in the Enumeration of Allowed Sequences for Different Structural Classes*, J. Mol. Biol. (1987) 193 775–791.

M. J. Sutcliffe, et al., *Knowledge Based Modelling of Homologous Proteins, Part II: Rules for the Conformations of Substituted Sidechains*, Protein Engineering, vol. 1, No. 5 (1987), 385–392.

Neena L. Summers, et al., *Construction of Side-chains in Homology Modelling Application to the C-terminal Lobe of Rhizopuspepsin*, J. Mol. Biol. (1989) 210, 785–811.

Alexei V. Finkelstein, et al., *A Search for the Most Stable Folds of Protein Chains*, Nature, (Jun. 6, 1991) vol. 351:497–499.

Christopher Lee, et al., *Accurate Prediction of the Stability and Activity Effects of Site-directed Mutagenesis of a Protein Core*, Nature (Apr. 11, 1991) 352: 448–451.

Christopher Lee, et al., *Prediction of Protein Side-Chain Conformation by Packing Optimization*, J. Mol. Biol. 217, (1991) 373–388.

S. Kirkpatrick, et al., *Optimization by Simulated Annealing*, Science, vol. 220, No. 4598 (May 13, 1983).

Richards, *Protein Folding Problem*, Scientific American (1991), vol. 265, p. 54.

Reid and Thorton, *Proteins*, (1989) vol. 5, pp. 170–182.

Holm L. and Sander C. (1991), "Database algorithm, for generating protein backbone and side-chain co-ordinates from a Catrace application to model building and detection of co-ordinate errors," *J. Mol. Biol.*, 218:183–184.

Primary Examiner—Roy N. Envall, Jr.
Assistant Examiner—Gita D. Shingava
Attorney, Agent, or Firm—Townsend and Townsend Khourie and Crew

[57] ABSTRACT

A method is provided for determining the packing conformation of amino acid side chains on a fixed peptide backbone. Using a steric interaction potential, the side chain atoms are rotated about carbon-carbon bonds such that the side chains preferably settle in a low energy packing conformation. Rotational moves are continued according to a simulated annealing procedure until a set of low energy conformations are identified. These conformations represent the structure of the actual peptide. The method may be employed to identify the packing configuration of mutant peptides.

26 Claims, 7 Drawing Sheets

Microfiche Appendix Included
(3 Microfiche, 159 Pages)

SEQUENCE LISTING (1) GENERAL INFORMATION:

SEQUENCE LISTING (i) APPLICANT: Lee, Christopher
  Subbiah, Subramanian
(ii) TITLE OF INVENTION: Prediction of Protein Side-Chain Conformation by Packing Optimization
(iii) NUMBER OF SEQUENCES: 2
(iv) CORRESPONDENCE ADDRESS:
  (A) ADDRESSEE: Jeffery K. Weaver
  (B) STREET: One Market Plaza, Steuart Tower, Suite 2000
  (C) CITY: San Francisco
  (D) STATE: California
  (E) COUNTRY: USA
  (F) ZIP: 94610
(v) COMPUTER READABLE FORM:
  (A) MEDIUM TYPE: Floppy disk
  (B) COMPUTER: IBM PC compatible
  (C) OPERATING SYSTEM: PC-DOS/MS-DOS
  (D) SOFTWARE: PatentIn Release #1.0, Version #1.25
(vi) CURRENT APPLICATION DATA:
  (A) APPLICATION NUMBER: US 07/823,790
  (B) FILING DATE: 21-JAN-1992
  (C) CLASSIFICATION:
(viii) ATTORNEY/AGENT INFORMATION:
  (A) NAME: Weaver, Jeffrey K.
  (B) REGISTRATION NUMBER: 31,314
  (C) REFERENCE/DOCKET NUMBER: 5490A-87
(ix) TELECOMMUNICATION INFORMATION:
  (A) TELEPHONE: 415-326-2400
  (B) TELEFAX: 415-326-2422
(2) INFORMATION FOR SEQ ID NO:1:
  (i) SEQUENCE CHARACTERISTICS:
    (A) LENGTH: 4 amino acids
    (B) TYPE: amino acid
    (C) STRANDEDNESS: single
    (D) TOPOLOGY: linear
  (ii) MOLECULE TYPE: peptide
  (xi) SEQUENCE DESCRIPTION: SEQ ID NO:1:

Glu Ala Thr Gly
1

(2) INFORMATION FOR SEQ ID NO:2:
  (i) SEQUENCE CHARACTERISTICS:
    (A) LENGTH: 6 amino acids
    (B) TYPE: amino acid
    (C) STRANDEDNESS: single
    (D) TOPOLOGY: linear
  (ii) MOLECULE TYPE: peptide
  (xi) SEQUENCE DESCRIPTION: SEQ ID NO:2:

Glu Asp Gly Gly Val Ile
1               5

PREDICTION OF PROTEIN SIDE-CHAIN CONFORMATION BY PACKING OPTIMIZATION

MICROFICHE APPENDIX

This specification includes microfiche Appendix having 3 sheets with 159 frames.

COPYRIGHT NOTICE

A portion of the disclosure of this patent document contains material which is subject to copyright protection. The copyright owner has no objection to the facismile reproduction by anyone of the patent document or the patent disclosure as it appears in the Patent and Trademark Office patent file or records, but otherwise reserves all copyright rights whatsoever.

BACKGROUND OF THE INVENTION

The invention relates to methods for mutating and determining the physical stability and conformation of peptides. The method predicts the structure of a peptide and the effects of mutations on the structure and the physical stability of a peptide.

Peptide folding and structure prediction is complex due to the large number of atoms in a typical peptide. The large size of a peptide chain, in combination with its large number of degrees of freedom, allows it to adopt an immense number of conformations. For example, a relatively small polypeptide of 100 residues may exist in up to $10^{30}$ conformations. Despite the multitude of possible conformations, many peptides, even large proteins and enzymes fold in vivo into precise three-dimensional structures. The peptide generally folds back on itself creating numerous simultaneous interactions between different parts of the peptide. These interactions result in a stable three-dimensional structure that provides unique chemical environments and spatial orientations of functional groups that give the peptide its special structural and functional properties, as well as its physical stability. The ability to predict peptide structures and stabilities from knowledge of the constituent amino acids would be highly desirable.

Earlier efforts at peptide structure prediction have focused on prediction of side-chain conformation (given knowledge of the position of the main chain) as a less complex but nonetheless important portion of the "Protein Folding Problem." (For a description of the "Protein Folding Problem," see Richards, *Scientific American* (1991), vol 265, pg. 54, which is hereby incorporated by reference for all purposes.) Numerous methods attempt to predict protein conformation from a knowledge of the primary sequence. Examples of these methods are embodied in programs such as "Homology" by Biosym, "Biograf" by BioDesign, "Nemesis" by Oxford Molecular, "SYBYL" and "Composer" by Tripos Associates, "CHARMM" by Polygen, "AMBER" by UCSF, and "MM2" and "MMP2" by Molecular Design, Ltd. This list is meant to be illustrative rather than exhaustive.

Accurate prediction of amino acid side-chain conformation from the peptide primary sequence and a model of the peptide main chain would be highly useful.

SUMMARY OF THE INVENTION

The invention provides a method for predicting the three dimensional conformation of a peptide. This method utilizes the understanding that amino acid side chains of a peptide adopt conformations that maximize favorable atom-atom contacts and minimize unfavorable contacts. With this principle, the method determines the energy of atom-atom interactions and adjusts the amino acid side chain conformations to minimize this energy.

Accordingly, in one aspect, the invention is directed to a method for determining the three-dimensional structure of a peptide having amino acid side chains extending from a defined main chain. Each amino acid side chain has predefined rotational degrees of freedom.

A preferred method includes steps of first constructing an initial three dimensional peptide conformation by placing the amino acid side chains in an initial three dimensional conformation. The side chains are then randomly rotated around predefined rotational degrees of freedom by a small rotational perturbation to produce a modified three dimensional peptide conformation and determining the interaction energy of the amino acid side chains for the modified peptide conformation. Finally, a three dimensional model of the peptide is created by reducing the side chain steric interaction energy by repeatedly moving the amino acid side chains and determining the interaction energy by the process of simulated annealing. In one embodiment, additional three dimensional models of the peptide are created by the above procedure and averaged to produce an average three dimensional model of the peptide.

In preferred embodiments, the step of rotating the amino acid side chains randomly will be conducted in increments of $-25°$ to $25°$. Preferably the angle of rotation will be between $-12°$ and $12°$, and most preferably between $-11°$ and $11°$. According to another preferred embodiment, interaction energy barriers are truncated to a predetermined maximum so that solution space may be completely explored.

Another method for determining the three dimensional structure of a peptide, according to the present invention, involves the steps of first constructing an initial three dimensional peptide conformation by placing each amino acid side chain in an initial three dimensional conformation. Next, the side chain steric interaction energy for the initial peptide conformation is determined. In preferred embodiments, the interaction energy will be truncated if it exceeds a predefined maximum. Finally, the full conformation space is searched for low energy peptide conformations by randomly rotating each of the amino acid side chains around respective predefined rotation degrees of freedom. This produces a modified three dimensional peptide conformation for which the side chain steric interaction energy is then calculated. Those peptide conformations having a sufficiently low energy represent a three dimensional model of the peptide.

In a preferred application of the present invention, a peptide is synthesized having the structure used to model a low energy or otherwise stable peptide. The stable peptide structure is identified from among a group of structures that are modelled according to the above procedure. Each of these structures will have at least one amino acid that is different from a corresponding amino acid in the other structures. At least one structure from among this group will be identified as having a suitable stability and thereafter synthesized by techniques that are well known in the art.

A peptide is an oligomer of amino acids attached in a linear sequence to form, for example, a protein or an enzyme. Peptides consist of a main chain backbone having the following general pattern:

$$H-(-NR-C^\alpha-CO)_n-OH$$

where n equals the number of amino acid residues in the peptide and $C^\alpha$ is the so-called alpha carbon of an amino acid. For nineteen of the twenty naturally occurring amino acids, R=H. The other, proline, is an imino acid and R=—$CH_2$—.

The primary sequence of a peptide represents the sequence of the constituent amino acids such as, for example, $NH_2$—Glu—Ala—Thr—Gly—OH. (SEQ. ID No: 1). The $NH_2$— and —OH moieties represent the amino and carboxyl terminii of the peptide, respectively, and also indicate the directionality of the peptide chain. The peptide's secondary structure represents the complex shape of the main chain and generally indicates structural motifs of different portions of the peptide. Common secondary structure includes, for example, alpha-helices, beta-sheets, etc. The tertiary structure of a peptide represents the three dimensional structure of the main chain, as well as the side chain conformations. Tertiary structure is usually represented by a set of coordinates that specifies the position of each atom in the peptide main chain and side chains and is often visualized using computer graphics or stereopictures. Finally, quaternary structure represents the three-dimensional shape and the interactions that occur between different peptide chains, such as between subunits of a protein complex.

Non-amino acid fragments are often associated with a peptide. Such fragments can be covalently attached to a portion of the peptide or attached by non-covalent forces (ionic bonds, van der Waals interactions, etc.). For example, many peptides which are bound in the cell membrane are used for cell recognition and have carbohydrate moieties attached to one or more amino acid side chains. Non-amino acid moieties include, but are not limited to, heavy metal atoms such as single molybdenum, iron, or manganese atoms, or clusters of metal atoms, nucleic acid fragments (such as DNA, RNA, etc.), lipids, and other organic and inorganic molecules (such as hemes cofactors, etc.).

The three-dimensional complexity of a peptide arises because covalent bonds in each amino acid can rotate. The conformation of a peptide represents a particular three-dimensional arrangement of atoms and, as used herein, is equivalent to its tertiary structure. Similarly, the conformation of an amino acid side chain is the three-dimensional structure of that side chain. In general, an amino acid side chain can assume many different conformations, with the exception of glycine which assumes only one. In preferred embodiments of the invention, the side chains of alanine and proline all have only one conformation.

As used herein, a side chain rotamer is a single conformation of the amino acid side chain. For an amino acid side chain having three rotational degrees of freedom, such as glutamic acid, a rotamer can either be specified as an ordered set of three numbers that defines the values for each rotational degree of freedom, or as an ordered set of coordinates that defines the three-dimensional position of each atom.

The absolute physical stability of a peptide represents the energy of the peptide in a particular conformation relative to the same peptide in an unfolded state. A peptide having a high physical stability is more stable in its folded state, relative to a peptide having a lower physical stability. In general, the absolute physical stability of a peptide is not determined (since the energy of the unfolded peptide is unknown), but its physical stability relative to a related peptide can be determined. An increase in the physical stability of a peptide generally results in an increase in thermal stability, although it could result in an increase in binding affinity, stability in salt solutions, pH stability, and other environmental conditions.

As used herein, "minimizing energy" of a peptide denotes the use of an appropriate method to increase the physical stability of the peptide by reducing its energy by altering its conformation. The resulting structure will have a lower energy (assuming, of course, that the method finds such a structure) relative to the starting structure, but will not necessarily have the global minimum energy. The term "minimized energy structure" or "minimized energy conformation" represents a structure that exists as a minimum in the energy surface—the minimum may be a local minimum or a global minimum.

DESCRIPTION OF THE PREFERRED EMBODIMENTS

I. Amino Acid and Peptide Structure

One aspect of determining peptide conformation is the prediction of two basic classes of degrees of freedom. The $\phi$-$\Psi$ torsions, which determine the folding of main chain atoms of the peptide, and the $\chi$ torsions, which specify the set of angles that defines the conformation of each amino acid side chain. These two sets of variables are closely coupled, because of the tremendous importance of side chain conformation and packing for the stability of the overall peptide conformation.

A preferred method of the invention determines the set of $\chi$ torsions, holding the $\phi$-$\Psi$ torsions substantially constant.

Figure 1:
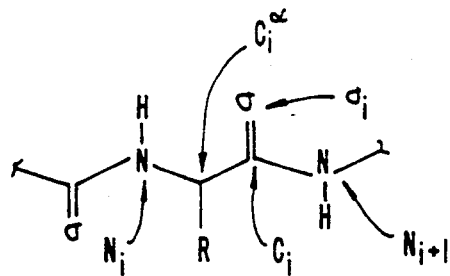
FIG. 1 illustrates the arrangement of atoms in a peptide backbone.

Peptides fall into the general class of polymers and are simply molecules generated from a sequence of amino acid residues connected in series. With reference to FIG. 1, the peptide backbone, or main chain, consists of a repeated sequence of atoms: an amide nitrogen $N_i$, the alpha carbon $C_i^\alpha$, and the carbonyl carbon $C_i$, where i represents the amino acid in the peptide sequence. The carbonyl oxygen, $O_i$, is attached to the carbonyl carbon and hydrogens are attached to both the amide nitrogen and alpha carbon. In principle, rotation can occur around any of the three bonds of the peptide main-chain. In practice, however, the bond between $C_i$ and $N_{i+1}$, the peptide bond, has partial double bond character that inhibits its rotation and in the absence of a strong force, $C_i^\alpha$, $C_i$, $O_i$, and $N_{i+1}$ lie in approximately the same plane.

Figure 2A:
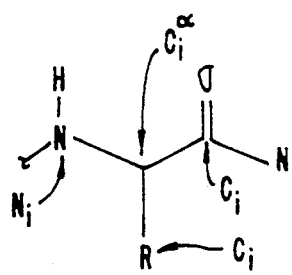
FIG. 2 illustrates (a) the general chemical structure of a naturally occurring amino acid, (b) the chemical structure of glycine, and (c) chemical structure of proline.
Figure 2B:
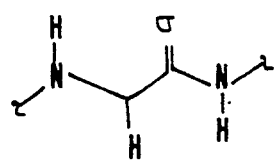
Figure 2C:
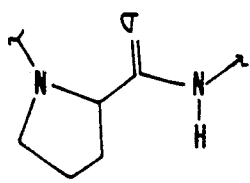

There are twenty common naturally-occurring amino acids, eighteen of which have the general structure shown in FIG. 2a, while glycine has the structure shown in FIG. 2b, and the remaining natural amino acid, proline, is shown in FIG. 2c. Referring to FIG. 2a, the first carbon of the side chain, which is attached to $C_i^{\beta 0}$, is the beta carbon, $C_i^{\beta 2}$. In preferred embodiments of the invention, the beta carbon of each side chain has a fixed position relative to the peptide main chain defined by $C_i^{\beta 0}$, $C_i$, $N_i$ and $O_i$. Thus, the position of the main chain specifies the position of the first atom of each side chain. By beta carbon, or $C^\beta$, we refer to the atom of a side chain attached to $C^\alpha$. In nineteen of the twenty natural amino acids, $C^\beta$ is a carbon, while for glycine $C^\alpha$ is a hydrogen.

Figure 3A:
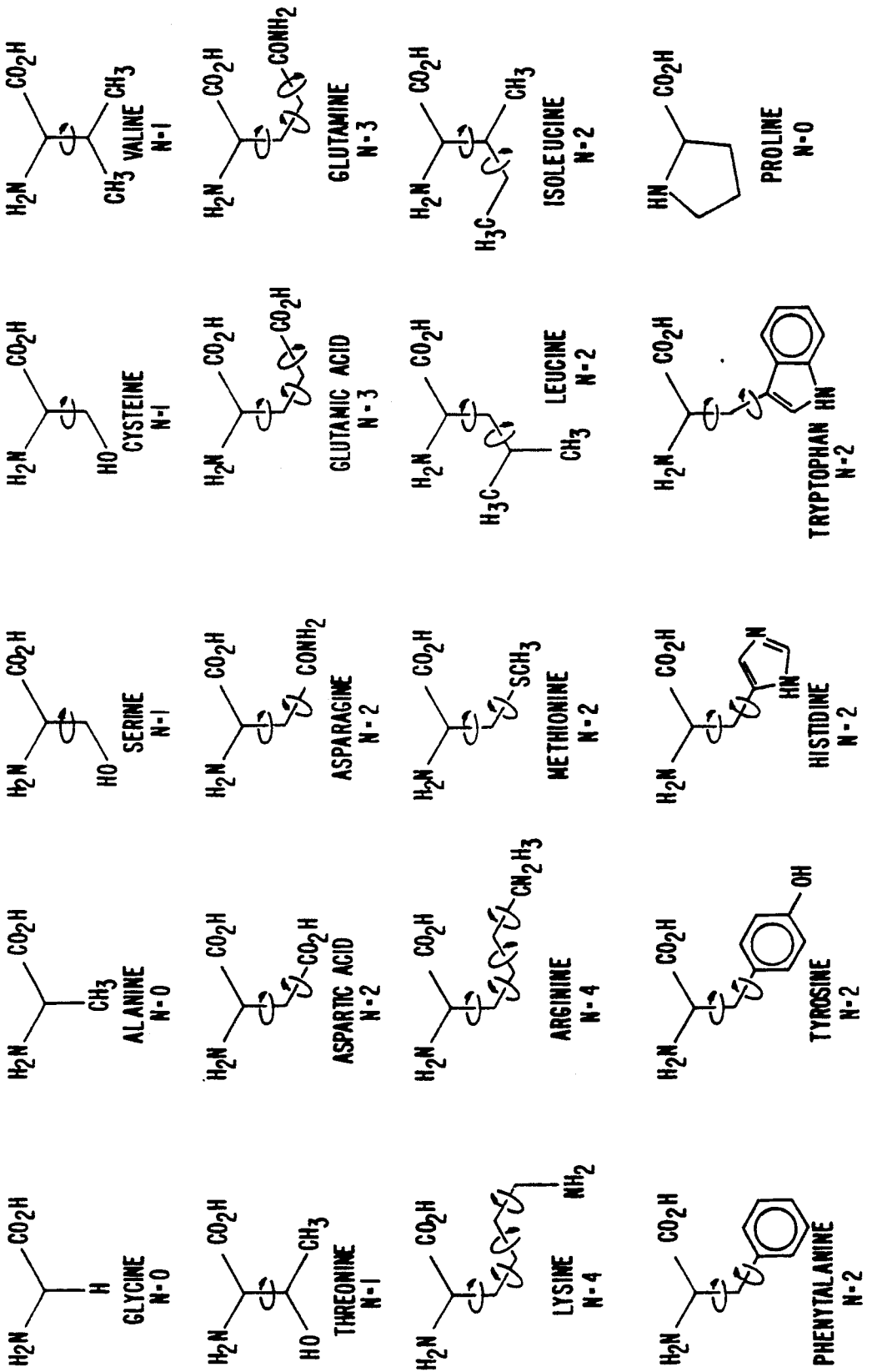
FIG. 3a illustrates preferred sets of rotational degrees of freedom for each naturally occurring amino acid.

Each side chain has unique physical and chemical properties, as is well known (see, Creighton "Proteins: Structure and Molecular Principles," W. H. Freeman and Company, New York, 1984, which is incorporated by reference for all purposes). The side chain of each amino acid can adopt a myriad of possible conformations, the number of which depends on the number of predefined rotational degrees of freedom. FIG. 3a illustrates a preferred set of rotational degrees of freedom for each amino acid. As defined in this set, rotations about a methyl group which has, in theory, a three-fold rotation axis (taking hydrogen atoms into account), and hydroxyl/sulfhydryl groups which have no rotational symmetry, are not included. The asymmetry introduced by the attached hydrogens is ignored as discussed below. Structurally simple amino acids, such as alanine and glycine, as well as the imino acid proline, consist of side chains that have no rotational degrees of freedom, while the side chains of more complex amino acids such as lysine and arginine have four.

Although only twenty amino acids are commonly used in vivo as protein building blocks, less common natural amino acids exist, as well as unnatural amino acids. Amino acids in these categories include enantiomers and diastereomers of the natural D-amino acids, oxyproline, cyclohexylalanine, norleucine, cysteic acid, methionine sulfoxide, ornithine, citrulline, omega-amino acids such as 3-amino propionic acid, 4-amino butyric acid, etc. All such amino acids can be incorporated into peptides by suitable methods known in the art, and the structure of a peptide having these uncommon amino acids can be determined when the structure and properties of the uncommon amino acids are known. Thus, as used herein, the term amino acid includes all natural amino acids coded by the genetic code, as well as uncommon natural amino acids and unnatural amino acids.

II. Nucleotide and Nucleic Acid Structure

Figure 3B:
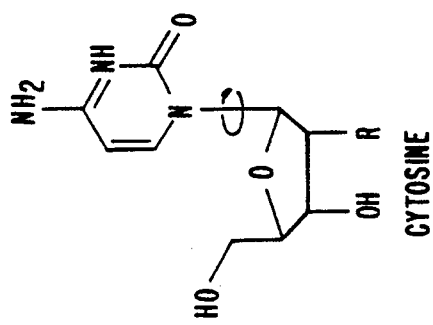
FIG. 3b illustrates the chemical structure of the five naturally occurring nucleotides.
Figure 3B:
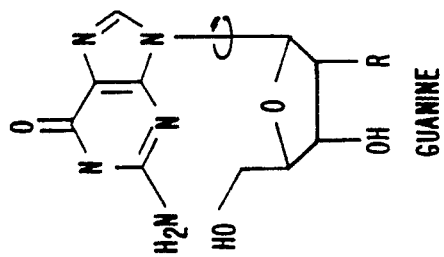
Figure 3B:
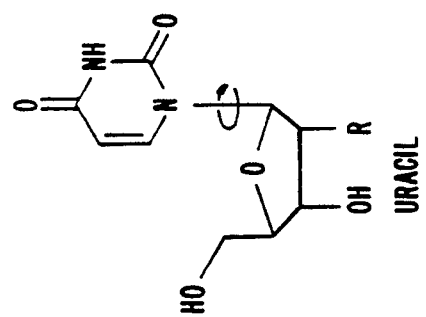
Figure 3B:
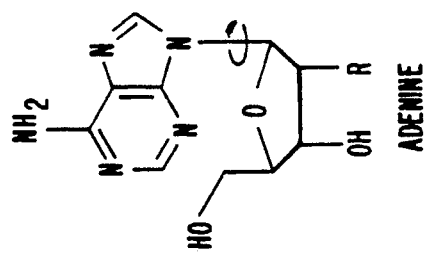
Figure 3B:
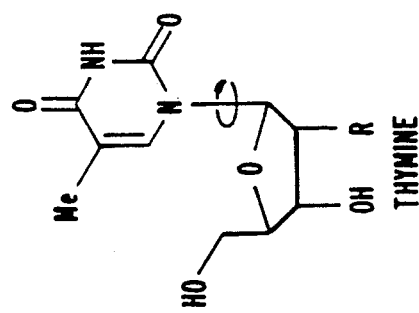

In addition to determining peptide structure, the invention method is suitable for determining the structure of poly-deoxyribonucleic acids (DNA) and poly-ribonucleic acids (RNA), as well as protein-DNA and protein-RNA complexes. The monomeric units of these biological polymers are the nucleotides, which are shown in FIG. 3b. The five common, naturally-occurring nucleotides adenine, guanine, cytosine, thymine, and uracil have the general structure consisting of a phosphate, a sugar, and a purine or pyrimidine base. Each of these nucleotides is planar, and has one rotational degree of freedom, as shown in FIG. 4. In addition, to the common, naturally-occurring nucleotides, oligonucleotides often contain other nucleotides such as Base Y, $N^2$-dimethyl guanosine, inosine, dihydrouridine, etc. Such nucleic acids are well known in the art (see. Cantor et al. "Biophysical Chemistry, Part I" (1980), pg. 155, which is incorporated by reference for all purposes). As used herein, nucleotide refers to the set of common and uncommon naturally-occurring nucleotides, as well as the set of unnatural nucleotides. In all such nucleotides, the sugar ring may be deoxyribose, ribose, or any suitable variation (such as, for example, in a 2-methyl nucleotide).

III. Prior Approaches to Peptide Structure Determination

As with the larger problem of predicting protein folding, the principal difficulty of predicting side-chain conformations (where the main chain atoms are held substantially fixed in space) is the enormous size of the solution space (i.e., number of possible permutations). Even considering side chain torsions as a set of rigid rotations divided into quantized 10° steps (so that each degree of freedom has $360°/10° = 36$ distinct possible rotational states), a peptide having n different $\chi$ torsions produces up to $36^n$ conformationally distinct peptides. For example, a five residue peptide with a total of ten $\chi$ torsions has $3.7 \times 10^{15}$ possible conformations that need to be evaluated to determine the low energy conformations. Thus, simultaneous optimization of multiple side-chains is a difficult and time-consuming operation.

A prior strategy to optimize the structure of peptide decreases the number of conformational permutations by limiting the number of conformations allowed for each side chain (see, Ponder et al. *J. Mol. Biol.* (1987) vol. 193, pg. 775, which is incorporated by reference for all purposes). This method allows each side chain to exist in only a small number of predetermined conformations, typically three to seven, and forbids free rotation of each amino acid torsion. Thus, for a five amino acid peptide where each side chain is constrained to five conformations, there are only 3125 possible permutations. This method, however, has an exponential dependence on the size of the problem (e.g., a 100-residue peptide that has side chains constrained to 5 conformations each requires examining $7.9 \times 10^{69}$ possible permutations).

Another approach predicted side chain conformations residue by residue and did not attempt to predict all side chain conformations simultaneously. The method weighs the side chain predictions intelligently and gradually assigned side chain conformations in order of most reliable to least reliable. Reid et al. (*Proteins* (1989) vol. 5, pg. 170, which is incorporated by reference for all purposes) used this method to predict side-chain conformations of flavodoxin with an overall root-mean-square (r.m.s.) error of 2.41 Å, compared with the X-ray crystal structure. Starting from the alpha carbon coordinates, they predicted the positions of other main-chain atoms, and manually examined and adjusted the structure using computer graphics to predict the conformation of the side-chains.

A third approach to predict peptide structure is exemplified by Karplus et al. (*Proc. Nat. Acad. Sci., USA* (1989) vol. 86, pg. 8237, which is incorporated by reference for all purposes) which uses a multiterm potential energy function to calculate the interaction energy between atoms in the protein. The minimization method used molecular dynamics and, as a method for predicting peptide structure, this method relies on a detailed structure as a starting point. Like the other methods, this method has an exponential dependence on the number of atoms considered in the calculation.

IV. Three-Dimensional Conformation of the Peptide Main Chain

The present method utilizes the three-dimensional structure of the peptide main chain as a starting point for predicting the conformation of the peptide side chains. Many suitable methods exist that provide this information. X-ray or neutron diffraction (hereinafter referred to as "diffraction") provides a detailed picture of the three-dimensional positioning of the peptide main chain. Diffraction methods are well known (see, for example, Cantor et al. "Biophysical Chemistry Vol. III" (1980) W. H. Freeman & Co., San Francisco, chapter 13, which is incorporated by reference for all purposes). Diffraction methods are based on the observation that many peptides crystallize into well-defined three dimensional crystal lattices which scatter impinging X-ray or neutron irradiation. Collection and analysis of the scattered beams, in conjunction with other experiments, produces the three dimensional structure of the crystal lattice. In the current state of peptide crystallography, to obtain the three dimensional structure generally requires use of auxiliary techniques such as isomorphous heavy metal replacement, multiple wavelength scattering, anomalous scattering, to supplement the collected scattered X-ray or neutron beam data (See Cantor et al. "Biophysical Chemistry Vol. III").

Coordinates for each atom of the peptide main chain are obtained once the electron density map of the peptide main chain has been solved. The electron density map of the peptide generally has an associated correlation coefficient and a resolution that represents the accuracy of the data and the amount of detail present, respectively. In accurate high resolution electron maps, structural elements such as the coordinates of main chain and side chain atoms are readily observed. Low resolution data generally includes the positions of the main chain atoms but does not, however, include side chain positions. The present method utilizes both high and low resolution diffraction data.

Other methods for determining the three-dimensional conformation of the peptide main chain suitable for use with the invention include, for example, nuclear magnetic resonance (NMR) spectroscopy and theoretical prediction. Structural determination by NMR spectroscopy involves three steps: identification and assignment of resonance signals of the spectra to individual nuclei, inter-nuclei distance measurements, and computation of the structure. Suitable NMR methods include, for example, one-dimensional proton ($^1$H) NMR spectroscopy, which is used to identify individual protons in a peptide, two-dimensional $^1$H NMR methods (including correlated experiments which rely on J-coupling) which provide interproton relationships using through-bond coupling, and the Nuclear Overhauser Effect (NOE) experiments which provide spatial relationships using through-space information (see Griesing et al. *J. Mag. Res.* (1989), vol. 73, pg. 574. which is incorporated by reference for all purposes.) Other NMR methods suitable for use with the present invention include the use of insensitive nucleus enhancement by polarization transfer (INEPT), two-dimensional Nuclear Overhauser spectroscopy (NOESY), rotating frame nuclear Overhauser effect spectroscopy (ROESY), reverse INEPT, totally correlated spectroscopy (TOCSY), heteronuclear multiple quantum coherence (HMQC), and suitable combinations thereof in conjunction with both homonuclear and heteronuclear experiments. These techniques are well known in the art (see Lecome, "NMR/X-Ray Workshop: An Overview" in "Techniques in Protein Chemistry II" (1991), pg. 337, Academic Press, Inc., San Diego, which is incorporated by reference for all purposes).

Use of the so-called Ramachandran contour diagrams provides a theoretical method of predicting the peptide main chain conformation. The Ramachandran contour diagram is based on the observation that unfavorable steric overlaps between main chain atoms can be excluded by evaluating the $\phi$-$\Psi$ torsions. (See, Cantor et al. "Biophysical Chemistry Part 1: The Conformation of Biological molecules" (1983), W. H. Freman and Co., San Francisco, ch. 5, which is incorporated by reference for all purposes.) Other applicable theoretical methods will be readily recognized by one of skill in the art.

The positions of all main chain atoms need not be initially determined. As described above, the carbonyl carbon, carboxyl oxygen, $C^\alpha$, and the amide nitrogen are generally constrained to lie in a plane. With this constraint and the knowledge of the positions of some of these atoms, and the amino to carboxyl direction, the remaining atoms of the peptide main chain can be constructed as known in the art (see, Kabsch, *Acta Cryst.* (1978) vol. A34, pg. 827, which is incorporated by reference for all purposes).

V. Primary Sequence of Peptide

In the context of the this specification it should be appreciated that the amino acids may be either L-optical isomers or D-optical isomers, but unless otherwise specified they will be the naturally occurring L- natural amino acids. Standard abbreviations for amino acids will be used, whether a single letter or three letters are used. The single letter abbreviations are included in Stryer, *Biochemistry*, 3rd Edition, 1988, which is incorporated herein by references for all purposes.

After the three-dimensional position of each main chain atom is determined, the primary sequence of the peptide is mapped onto this peptide conformation. A primary sequence is mapped onto a main chain by assigning a side chain to a particular main chain $C^r$. For example, in the peptide sequence EDGGVI, (SEQ. ID No: 2) a glutamic acid side chain, conventionally designated by the symbol E, is assigned to the first alpha carbon of the peptide, $C_1^\alpha$ of the peptide, an aspartic acid side chain (symbol D) is assigned to the second alpha carbon peptide, $C_2^\alpha$, glycine (symbol G) side chains to $C_3^\alpha$ and $C_4^\alpha$, etc. In addition to assigning the identity of each side chain, the three-dimensional position of $C^\beta$ for each side chain is determined according to predefined relationships between the atoms of the main chain backbone. A preferred set of parameters describing the relationship between $C_i^{60}$, $O_i$, $N_i$ and $C_i^\beta$ are listed in the attached appendix, file: Plib. Mapping of the primary sequence of the peptide onto the main chain backbone identifies the alpha carbons associated with each amino acid and it positions $C^\beta$ for each residue in a predetermined position relative to the main chain backbone.

The primary sequence of a peptide represents the identity and sequence of the peptide's amino acids and may be obtained by techniques well-known in the art of peptide chemistry and molecular biology. Suitable methods for determining the primary sequence include, but are not limited to, direct determination from X-ray crystal data, peptide sequencing, and gene sequencing.

Determination of a peptide's primary sequence from X-ray data consists of tracing the electron density map of the peptide and assigning the side chains to each residue based on the electron density and knowledge of side chain structure.

A second and more conventional method of primary structure determination is peptide sequencing and is well known in the art. For example, Edman degradation, which exemplifies peptide sequencing, removes a single amino acid from the amino terminus of the peptide. Edman degradation generally uses phenyl isothiocyanate which reacts with the uncharged terminal amino group of the peptide to form a phenylthiocarbamoyl derivative. Under mildly acidic conditions, a cyclic derivative of the terminal amino acid is released into the solution leaving the intact peptide shortened by one amino acid. The liberated cyclic compound is a phenylthiohydantoin amino acid that is identified by chromatography (See Stryer "Biochemistry" (1975) W. H. Freeman & Co., pg. 24, which is incorporated by reference for all purposes). This process is repeated to identify subsequent amino acids. Another peptide sequencing method uses isothiocyanate under different conditions to sequence the peptide from the carboxyl terminus (see Schlack et al. Z. Physiol. Chem. (1926) vol. 26, pg. 865; Bailey et al. Tech. Prot. Chem. II (1991) pg 115; and Boyd et al. Tet. Lett. (1990) vol. 27, pg. 3849; which are all incorporated by reference for all purposes). Other methods of peptide sequencing include cyanogen bromide degradation, trypsin digestion, staphylococcal protease, etc., alone, or in combination with the above described techniques, as is well-known in the art.

Gene sequencing is another common method for obtaining a peptide primary sequence. This method involves isolating the gene encoding the peptide, sequencing the gene, converting the resulting four-nucleotide code of nucleic acids to the 20-amino acid code of peptides.

Methods for gene isolation are well known in the art (see, for example, Sambrook et al. "Molecular Cloning: A laboratory Manual" 2d ed., (1989) Cold Spring Harbor Press which is herein incorporated by reference). In general, the methods start with production of a cDNA library from isolated mRNA and insertion into a replication vector (for an overview of gene cloning, see Watson et al. "Recombinant DNA: A Short Course," W. H. Freeman & Co., New York, 1983, which is incorporated by reference for all purposes). Insertion and expression of the library in a suitable host, followed by screening (such as by hybridization with a labeled probe) identifies host cells containing the vector containing the gene that encodes the peptide. Such cells can be isolated and their DNA isolated and sequenced.

Methods for sequencing genes are well known in the art, (see for example, Sambrook et al. "Molecular Cloning: A laboratory Manual" 2d ed., (1989) Cold Spring Harbor Press, chapter 13, which is herein incorporated by reference. In general, two sequencing techniques are commonly used: the enzymatic method of Sanger et al. and the chemical degradation method of Maxam and Gilbert. Although very different, these two methods generate separate populations of radiolabeled oligonucleotides that begin from a fixed point and terminate randomly at a fixed residue or combination of residues. In both methods, each nucleotide base in the oligonucleotide has an approximately equal chance of being the terminus, and each population consists of an equal mixture of oligonucleotide fragments of varying lengths. This population of oligonucleotides is then resolved by electrophoresis under conditions that can discriminate between individual olignucleotides differing in length by as little as one nucleotide. When the population is loaded into adjacent lanes of a sequencing gel, the order of nucleotides along the DNA can be read directly from an autoradiographic image of the gel.

Once the primary sequence of the peptide and structure of the peptide main chain are known, amino acid side chains are mapped onto the main chain backbone. As used herein, the term "mapping" refers to the process of identifying the amino acid side chain for each alpha carbon of a peptide main chain. This step is necessary to associate the correct side chain with each residue's alpha carbon when only the main chain backbone structure is available. For example, in cases where the position of the main chain backbone structure is determined by low resolution crystallography, the identity of each residue is not obtained. Use of gene sequencing, however, can provide the primary sequence of the peptide, which is used to specify the amino acid side chain attached to each alpha carbon on the main chain backbone.

A second aspect of sequence mapping involves specifying the three dimensional position of the beta carbon for each side chain. As described above, the beta carbon for each amino acid has a predefined spatial relationship relative to the main chain atoms. This relationship is used when the position of the beta carbon is unknown.

VI. Potential Energy Function

The conformation energy of a peptide can be modelled in many ways, ranging from potential energy functions having a single van der Waals interaction term, to potential energy functions having many terms that account for torsional biasing, electrostatic interactions, hydrogen bonding, hydrophobic interactions, entropic destabilization, cystine bond formation, and other effects.

Steric interactions between atoms, also known as van der Waals interactions, may be represented by the Lennard-Jones potential energy function, which has the form:

$$E = \epsilon_0 [(r_0/r)^{12} 3] \, 2(r_0/r)^6].$$

where r is the interatomic distance and $r_0$ and $\epsilon_0$ are empirical parameters describing, respectively, the equilibrium interatomic distance and the depth of the energy well for the van der Waals interaction of the pair of atoms. Table 1 presents the preferred values of these empirical parameters used in the preferred embodiment of the invention. No attempt has been made to optimize these parameters. As mentioned above in conjunction with the predefined rotational degrees of freedom, hydrogens atoms attached to both main chain and side chain atoms are not included in this molecular representation. In order to compensate for this, the van der Waals radius of each atom that has attached hydrogens is slightly augmented.

The van der Waals force is an electrostatic interaction arising from an instantaneous asymmetric electron distribution, which causes a temporary dipole. This transient dipole induces a complementary dipole in a neighboring atom to stabilize the transient dipole. An instant later the dipoles are likely to be reversed resulting in an oscillation and a net attractive force. At one extreme (as r tends to infinity), atoms do not interact and have no stabilizing or destabilizing effect on one another. At the other extreme (as r tends to zero) the electrostatic repulsion between atoms becomes strong and dominates other stabilizing effects. The Lennard-Jones potential becomes infinite, which physically corresponds to superimposing two atoms. These infinite energy barriers prevent methods based on biased random walks, such as simulated annealing, from traversing solution space when the step size of the walks is insufficient to cross them in one step. Recognition of this problem is a major feature of the present invention. Many techniques that permit the potential barriers to be hurdled may be employed. Preferably, however, these barriers are truncated. In a preferred embodiment of the invention, the maximum value is between about 4 and 15 kcal/mol and most preferably about 7 kcal/mol for each pairwise interaction. Any potential barrier greater than this maximum is replaced with a smaller maximum value, preferably between about 4 and about 15 kcal/mol.

TABLE 1

| Energetic parameters used for side-chain predictions | | | |
|---|---|---|---|
| Atom$_1$ | Atom$_2$ | $r_0$(Å) | $\epsilon_0$(kcal/mol) |
| C | C | 4.315 | 0.0738 |
| C | O | 3.916 | 0.0738 |
| C | N | 4.058 | 0.1746 |
| C | S | 4.315 | 0.0738 |
| O | O | 3.553 | 0.1848 |
| O | N | 3.683 | 0.2763 |
| O | S | 3.916 | 0.1168 |
| N | N | 3.817 | 0.4132 |
| N | S | 4.058 | 0.1746 |
| S | S | 4.315 | 0.0738 |

Figure 4A:
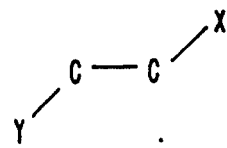
FIG. 4a–4b schematically shows the torsion about a carbon-carbon single bond.
Figure 4B:

Other forces exist between atoms of the peptide. For example, a torsional potential energy function models the interaction of linear four-atom sequences, such as Y-C-C-X. (See Streitwiser et al. "Organic Chemistry," 2d ed., Wiley & Sons, pg. 70 (1987) for a description of torsions about a carbon-carbon single bond). FIG. 4 schematically shows a torsion about a carbon-carbon single bond. FIG. 4a is a stick representation of Y-C-C-X, while FIG. 4b shows torsion $\chi$ in a view along the C—C bond. Suitable torsional potentials $\chi$ have the form:

$$E_{torsion} = K \cos[n(\chi - d)]$$

where n and d are constants (typically n=3 and d=0) where K is a constant that is typically about 1 to about 5 kcal/mol (preferably about 1.5 kcal/mol) and $\chi$ is the torsion angle between the groups attached to the two central carbon atoms. The magnitude of the interaction, K, depends on the individual identities of all groups attached to the central carbons. In general, when the atoms X and Y are large, K is also large. The torsional potential as expressed above represents the tendency for groups attached to a central carbon-carbon single bond to adopt a trans or gauche conformation. The potential is applied to all rotational degrees of freedom for each amino acid residue, except for $\chi_2$ of phenylalanine, tyrosine, histidine, and tryptophan. Since these involve an sp$^2$ hybridized carbon, they require a more complex torsion potential that accounts for the two-fold rotational symmetry of the planar ring.

In addition to the van der Waals and torsional potentials, other forces influence the conformation of a protein. For example, the electrostatic force that occurs between any two charged atoms takes the following form, which assumes that the two atoms may be approximated as point charges:

$$E_{electrostatic} = Z_A Z_B / Dr^2,$$

where r is the interatomic distance between two charged atoms, A and B; $Z_A$ and $Z_B$ equal the respective charges on the two atoms; and D is the dielectric constant of the environment around atoms A and B. As is well known, the force between two charges of the same sign is repulsive while the force between charges of opposite signs is attractive. This type of electrostatic interaction has the greatest influence on charged residues, such as lysine, arginine, glutamic acid, aspartic acid, etc. Inclusion of an electrostatic energy term requires assignment of a charge to each atom. As is well known in the art, the effective charge of an atom depends on its surrounding environment including such factors as, for example, pH, accessibility to water, the polarity of the solvent, and the presence of other charges.

Other types of electrostatic forces influence peptide structure as well. For example, dipole moments, which describe partial charges on atoms, occur in an uncharged, but polar groups of atoms. The electrostatic potential described by such dipole moments are well known and may be implemented as is known in the art. Another type of primarily electrostatic interaction is the hydrogen bond, which occurs when a hydrogen atom is shared between a proton donor and a proton acceptor. Hydrogen bonds stabilize pairs of polar moieties having hydrogen atoms to share and donate, such as between a serine hydroxyl group and the carbonyl carbon of an amide group, or between an acid group such as the carboxyl of a glutamic acid and water. The potential energy terms for both dipole and hydrogen bond interactions are well known in the art (see Cantor et al.).

Hydrophobic interactions are destabilizing noncovalent interactions between an atom having hydrophobic character and one having hydrophilic character. For example, large hydrophobic interactions occur between the polar, aqueous environment of the solvent and nonpolar residues of the peptide, such as valine, leucine, isoleucine, phenylalanine, etc. As applied to prediction of side chain conformations, hydrophobic interactions result in a tendency for nonpolar side chains to avoid interaction with solvent. Potential energy functions representing hydrophobic interactions are well known in the art and are used in some preferred embodiments to increase the prediction accuracy of hydrophobic side chains that happen to be exposed to solvent on the surface of the peptide.

Other energetic terms influence the overall conformation of a peptide and contribute to the overall potential energy function (see, for example Dill *Biochemistry* (1990), Vol. 29, pg. 7133, which is incorporated by reference for all purposes). For example, entropic terms, which account for the decrease in rotational and other degrees of freedom in the transition from unfolded to folded peptide are suitable for inclusion into the conformational energy calculation.

In a preferred embodiment of the invention, the physical stability of a peptide is modelled by a potential energy function having only a van der Waals energy term for simplicity. In other preferred embodiments, one or more of the previously-described energy terms are added.

VII. Conformation Energy Minimization

The invention method moves peptide side chains to maximize favorable interactions and minimize unfavorable ones. A major force influencing side-chain conformation is mediated by the necessity of avoiding steric overlap. One aspect of the present invention predicts side chain conformations by minimizing the steric packing interactions. A preferred embodiment of the invention predicts side chain positions by simultaneously finding side chains conformations that have a low steric energy. Such side chain conformations correspond physically to a peptide conformation having side chains well-packed. Finding these side chain conformations requires an efficient search and minimization strategy to locate energy minima in a very large solution space.

To minimize the conformation energy of a peptide, the present method uses the simulated annealing algorithm (Metropolis et at. *J Chem. Phys.* (1953) vol. 21, pg 1087, and Press et al. "Numerical Recipes in C", (1986) pg. 326, which are incorporated by reference for all purposes), which has been used for a variety of non-polynomial-complete optimization problems (Kirkpatrick et al. *Science* (1983) vol. 220, pg. 1983; Van Hemmen et al., *Lecture Notes in Physics* (1983) vol. 192; Brunger, *J Mol. Biol.* (1988) vol. 203, pg. 803; Subbiah & Harrison, *Acta Crystallogr. sect. A.* (1989) vol. 45, pg. 337, which are all incorporated by reference for all purposes). This algorithm solves such problems in a fraction of the computing time required for typical systematic searches based on algorithms such as steepest descent and other gradient driven methods.

The present method searches the large solution space by recognizing that every point in a sufficiently "smooth" (that is, continuous) solution space does not need to be evaluated to locate the general regions of energy minima. Thus, if the energy function that describes the solution space is sufficiently continuous and exhibits smooth trends, energy minima can be located by traversing paths across the solution space. The observed trends are then used to direct the search to those regions where minima are likely to be found.

The simulated annealing algorithm exemplifies this approach. In general, simulated annealing uses a random walk to traverse the solution space, with a bias towards minimal energy zones. At each step of the random walk a small, random perturbation from the current position is selected as a move, and the energy change (aE) associated with making this move is calculated. If the energy change is less than or equal to zero ($\Delta E \leq 0$), then the move is accepted. A random move having $\Delta E > 0$, however, is accepted with an acceptance probability of:

$$p = e^{-\Delta E/T},$$

where T is the "annealing temperature." Thus, the larger the value of $\Delta E$, the smaller the acceptance probability. On the other hand, large, positive values for T increase the acceptance probability for a given value of $\Delta E$.

In the annealing procedure, the random walk is started with a large T, so that the probability of acceptance for an energetically unfavorable move is close to unity ($p \approx 1$), regardless of the magnitude of $\Delta E$. In this temperature regime, the walk is unconstrained. Over the course of the random walk, however, T is gradually reduced, thereby biasing the walk towards lower regions of solution space having lower energy. The simulated annealing algorithm corresponds to randomly walking over the energy landscape, gradually reducing the rate of "escape" from the energy minima encountered. Throughout the minimization, structures encountered during the random walk having low energies are recorded. Applied properly, this algorithm results in a random walk that continuously passes through regions having most of the major energy minima and gradually increases the fraction of time spent in the deeper minima. If the temperature is reduced slowly enough, the procedure will spend most of the time walking around the region of solution space containing the deepest minimum.

For simulated annealing to find the deepest energy minimum, the random walk must traverse the solution space. It must sample the majority of values in every dimension, rapidly and without impediment, to ensure sufficient sampling of all regions. Large energetic barriers that separate energy minima can prevent the random walk from sufficiently exploring the solution space to locate the deepest minimum. Thus, either such barriers must be removed, or a mechanism must be used to traverse any such barriers. As described above in conjunction with van der Waals interactions, the infinite barriers that correspond to the singularity in the Lennard-Jones potential are truncated to allow traversal of the solution space. In a preferred embodiment, these barriers are truncated to 7 kcal/mol, although different values may be used, depending on the step size used in the random walk.

The problem of not sufficiently traversing the solution space may also be caused by lowering the annealing temperature, T, too rapidly. Rapid temperature reduction prevents the random walk from crossing the energy barriers trapping it in a local minima before a sufficient number of low energy structures have been encountered. To prevent this type of trapping, the annealing temperature is lowered in small temperature steps. This permits control of both the number of random walk moves per temperature-step. In a preferred embodiment, the annealing temperature is decreased by 2% during each temperature step.

The number of moves during each temperature step is chosen to guarantee extensive sampling and repeated traversal of the solution space. As is known, the rootmean-square (r.m.s.) deviation of a random walk of n unitary steps is $n^{\frac{1}{2}}$ and, therefore, the number of steps needed to generate an r.m.s. deviation d equals $d^2$. Thus, the desired r.m.s. deviation of each degree of freedom is first determined and the number of necessary steps is calculated. In a preferred embodiment, each degree of freedom is moved in 10 degree increments, with a 50% probability of moving a given torsion on each step. Thus, the number of random steps necessary to generate a 180° average deviation is $(180/10)^2/(0.50)=648$. In preferred embodiments, 10,000 move-steps during each temperature step are used to sample the solution space, and gives an average of approximately 15 traversals (i.e. oversampling by 15-fold) of the solution space during each temperature step. If a different step size is used then a corresponding change to the number of steps is made to ensure sufficient oversampling.

During the random walk, in each move-step, all side-chain torsion angles are randomly moved either $-10°$, 0° or $+10°$ as rigid rotations, with all bond lengths and angles held to predetermined equilibrium values (see Table 3 of Levitt, J. Mol Biol. (1983), vol 170, pp. 723-764, which is incorporated by reference for all purposes). However, other step sizes may be employed depending upon the application. Where less accuracy is necessary, larger (more course) steps may be taken. In some instances, the step size may be 12° or even as much as 25°.

In a preferred embodiment, the invention method contains several features to enhance its ability to seek minima and escape energetic "traps." To improve the method's ability to locate conformations in which all side-chains are well-packed, a separate algorithm evaluates the conformations of the individual residues. After every move, the method calculates each residue's total van der Waals interaction with its surroundings. If this energy is less than a predetermined threshold good packing value, the residue is placed in refinement mode that inhibits (but does not prevent) movement. For the next 1000 steps, the probability of a side chain in refinement mode moving is reduced 2-fold. In effect, this algorithm gently constrains well-packed residues, while seeking better conformations for side chains that are not yet well-packed. This method increases the speed in finding the global minimum.

For prediction problems larger than about 5 residues, the random walk typically becomes trapped in local minima at temperatures well above those needed to seek the global minimum. To avoid this problem and ensure that the random walk over-samples conformation space, the move algorithm slowly increases its move size in predetermined increments (for example, from 10° to 20° to 30° etc.) whenever a degree of freedom becomes trapped in a minimum (i.e. when the program fails to find a single acceptable move in over 100 consecutive steps), gradually enlarging the range of its allowed moves until it finds an acceptable move. The move size is then reset to normal.

VIII. Processing Technique

Figure 5:
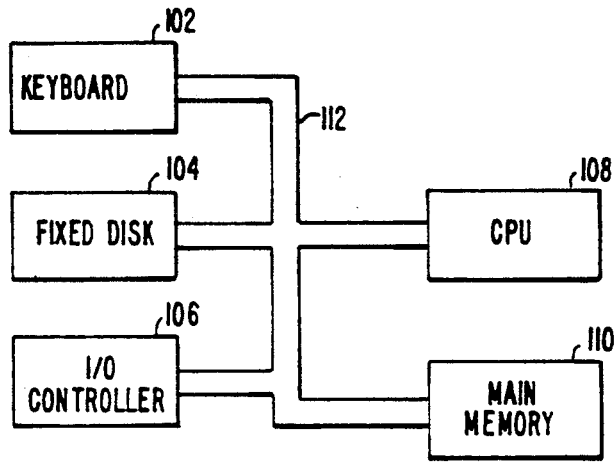
FIG. 5 illustrates a digital computer system that may be used to implement some aspects of the present invention.

The invention may be embodied on a digital computer system such as the system 100 of FIG. 5, which includes a keyboard 102, a fixed disk 104, a display monitor 104, an input/output controller 106, a central processor 108, and a main memory 110. The various components communicate through a system bus 112 or similar architecture. The user enters commands through keyboard 102; the computer displays images through the display monitor 104, such as a cathode ray tube or a printer. In preferred embodiments, an appropriately programmed computer, such as a Silicon Graphics Iris 4D/240GTX is used. Other computers, however, may be used in conjunction with the invention. Suitable computers include mainframe computers such as a VAX (Digital Equipment Corporation, Maynard, Mass.) or Cray Supercomputer (Cray Research), multi-processor computers such as those produced by Thinking Machines (Cambridge, Mass.) workstations such as the Sun SPARC (Sun Microsystems, Sunnyvale, Calif.) or Apollo workstations (Hewlett Packard, Cupertino, Calif.), personal computers such as MacIntosh computers (Apple Computer, Cupertino, Calif.) or IBM or IBM compatible personal computers.

Preferred internal processes of the prediction method generally consist of a setup routine which loads data and performs preliminary data analysis, a minimization routine that minimizes the conformation energy of the peptide, and post processing routines that analyze data from the minimization routines and predicts a peptide conformation. Preferred processes will be described in detail with reference to the flow charts in FIG. 6.

Data for each residue type was, in one embodiment, stored in a residue description having the following form:

```
res ILE natom:8
atom N  -1 charge -0.33 vdw 3.81700 0.41320
atom CA -1 charge 0.00 vdw 4.31500 0.07582
atom C  -1 charge 0.38 vdw 4.31500 0.07582
atom O  -1 charge -0.38 vdw 3.55300 0.18480
atom CB  0 charge 0.00 vdw 4.315 0.07582
atom CG1 1 charge 0.00 vdw 4.315 0.07582
atom CG2 2 charge 0.00 vdw 4.315 0.07582
atom CD1 3 charge 0.00 vdw 4.315 0.07582
bond ILE N ILE CA 1.48
bond ILE CA ILE N 1.48
ang ILE C ILE CB ILE CB 113.65
genbond ILE CA ILE CB 1.56
bond ILE C ILE CA 1.53
bond ILE C ILE O 1.25
ang ILE CA ILE CB ILE CG1 111.61
ang ILE CA ILE CB ILE CG2 112.57
genbond ILE CB ILE CG1 1.54
ang ILE CG1 ILE CB ILE CG2 110.77
genbond ILE CB ILE CG2 1.57
ang ILE CB ILE CG1 ILE CD1 117.80
genbond ILE CG1 ILE CD1 1.53
bond ILE CG2 ILE CB 1.57
bond ILE CD1 ILE CG1 1.53
twist ILE N ILE CA ILE C ILE CB -126.33
tor ILE N ILE CA ILE CB ILE CG1 0.00 <dof> 1.5 3.0 0.0
twist ILE CA ILE CB ILE CG1 ILE CG2 -125.44
tor ILE CA ILE CB ILE CG1 ILE CD1 0.00 <dof> 1.5 3.0 0.0
```

This residue description contains four major sections. The first line indicates the residue type (i.e. Isoleucine-=ILE) and number of atoms (excluding hydrogens) in the residue. The next section describes the atoms by type, the movement order, and the van der Waals (Lennard-Jones) constants. For example, the entry:

```
atom N  -1 charge -0.33 vdw 3.81700 0.41320
``` specifies that a nitrogen atom (atom N) belongs to the main chain and is not moved ($-1$), has a partial charge of $-0.33$, and has the Lennard-Jones constants $r_0=3.81700$ and $\epsilon_0=0.41320$. In contrast the entry:

```
atom CG2 2 charge 0.00 vdw 4.315 0.07582
``` specifies that the side-chain gamma-2 carbon (CG2) is built second (2), has no charge, has $r_0 = 4.31500$ and $\epsilon_0 = 0.07582$.

The third section of the data describes the bond lengths and bond angles of the residues in a local frame of reference. For example, the entries,

```
bond ILE N ILE CA 1.48
bond ILE CA ILE N 1.48
ang ILE C ILE CB ILE CB 113.65
genbond ILE CA ILE CB 1.56
``` illustrate the different types of indicators. "bond ILE N ILE CA 1.48" specifies that the bond length between the amide nitrogen and $C^\alpha$ is 1.48 angstroms. "anq ILE C ILE CA ILE CB 113.65" indicates that the angle defined by the carbonyl carbon, $C^\alpha$, and $C^\beta$, measured with $C^\alpha$ as the center is 113.65°. "genbond ILE CA ILE CB 1.56" indicates that a bond needs to be generated between $C^\alpha$ and $C^\beta$ that is 1.56 angstroms long.

Finally, the fourth section defines the three dimensional angular relationships between different atoms.

```
twist ILE N ILE CA ILE C ILE CB -126.33
tor ILE N ILE CA ILE CB ILE CG1 0.00 <dof> 1.5 3.0 0.0
```

The "twist" relationship is shown in FIG. 7 and describes the relationship of an atom with respect to a set of three other atoms. As shown in FIG. 7a, the three atoms N, $C_\gamma$ and C of the ILE residue uniquely define a plane that pass through the atoms. "Twist" 30 defines the angle that the fourth atom makes with this plane, as shown in FIG. 7b. "Tor" 25, on the other hand, is shown in FIG. 7c-d and defines the torsional angle between the atoms N and CG1, about the bond formed by CA and CB. Accompanying a "tor" is the <dof> indicator which specifies that there is a rotational degree of freedom between atoms CA and CB. Finally, the entry also lists the parameters of the torsional potential $E_{tor} = K\cos[n\chi - d]$. In this case, $K = 1.5$ kcal/mol, $n = 3.0$ and $d = 0.0$, indicating a three-fold torsional potential having a maximum interaction of 1.5 kcal/mol for a full eclipsed structure.

These data were stored in the file Plib, attached hereto as appendix A. The values for each amino acid were chosen to simplify the calculation—no attempt was made to optimize these values. It will be apparent to one of skill in the art that these values may be optimized to potentially achieve more accurate results.

The initial data, which represent the main chain conformation, includes data for each atom in the peptide main chain such as the three dimensional position and its chemical identity (for example, whether the atom is a carbon, nitrogen, oxygen, etc.). Such data comes from a variety of sources. As described above, diffraction, NMR, theoretical prediction or another suitable method may provide the main chain coordinates and identities. The main chain coordinates for peptides described herein, however, are derived from the Standard Brookhaven Protein Data Bank (PDB), which is well known in the art.

Figure 6A:
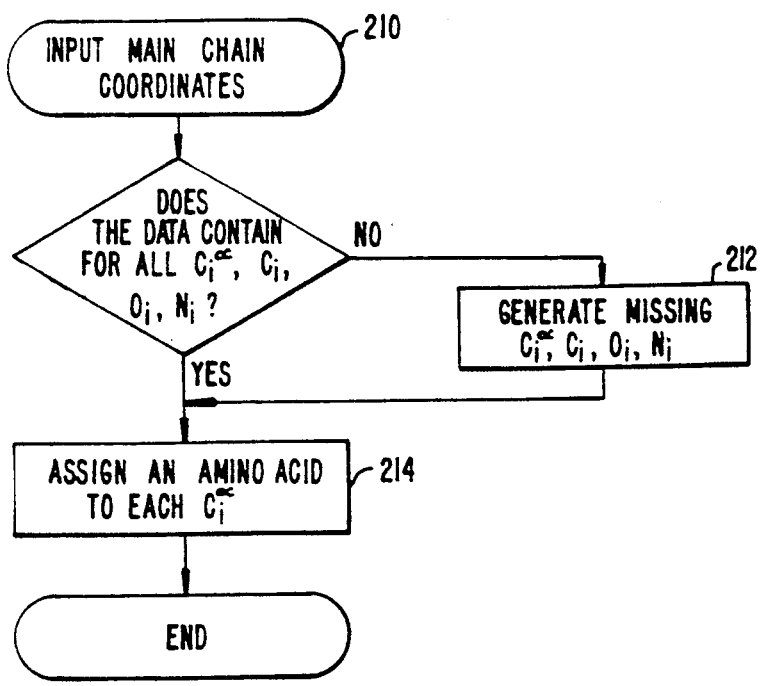
FIG. 6a shows the procedure used to load the main chain coordinates and amino acid sequence of the peptide to be modelled.

A preferred method of data input is described with reference to FIG. 6a. As described above, if an incomplete set of main chain coordinates is supplied as input data at step 210 (for example, only $C^\alpha$ positions), an optional process step 212 supplies the coordinates and the atom types for the missing main chain atoms. Such a process calculates, based on the positions of $C^\alpha$ and the amino to carboxyl direction, the positions of the carbonyl carbon and oxygen, and the amino group. After the positions of all main chain atoms have been defined, the primary sequence of the peptide is mapped onto the main chain. The primary sequence is merely a sequence of data representing the amino acid sequence. The mapping associates an amino acid side chain with each $C_i^\alpha$, as shown in step 214.

Figure 6B:
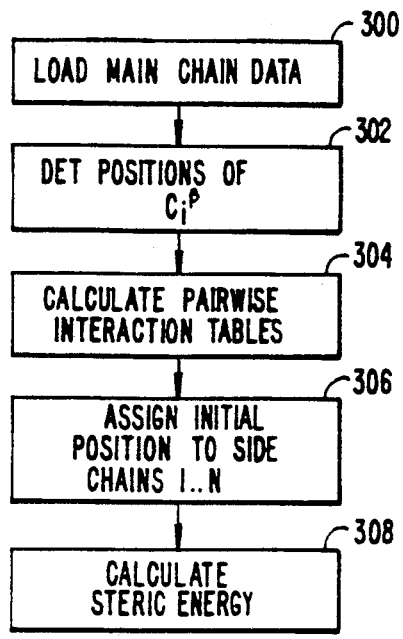
FIG. 6b schematically illustrates the set-up and pre-calculation steps employed in some methods of the present invention.
Figure 6C:
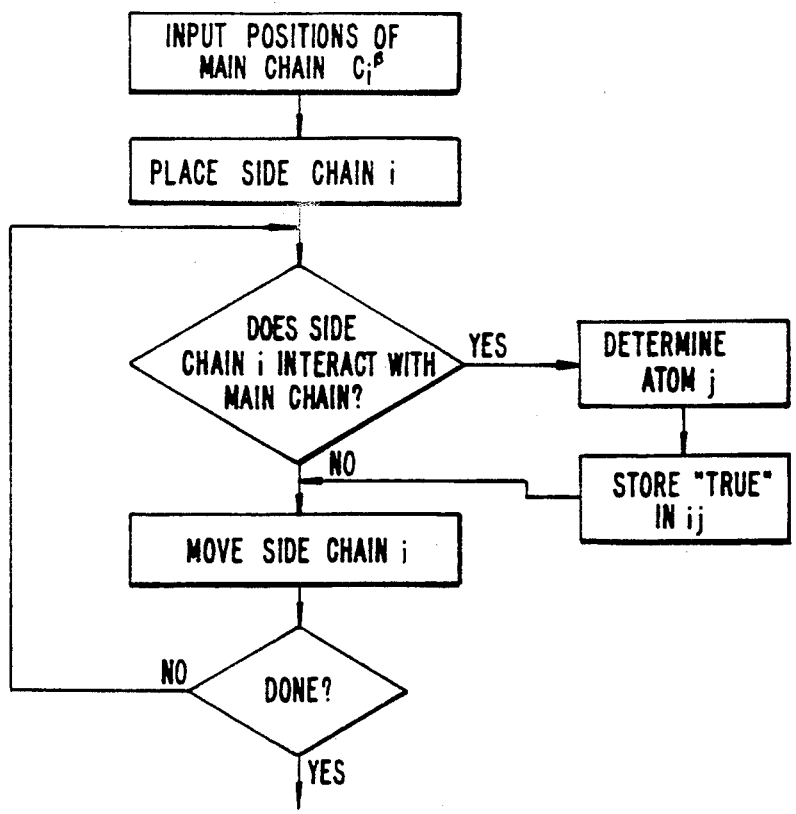
FIG. 6c schematically illustrates the preparation of lists of interactions between side chains and the main chain, and between a given side chain and other side chains.
Figure 6D:
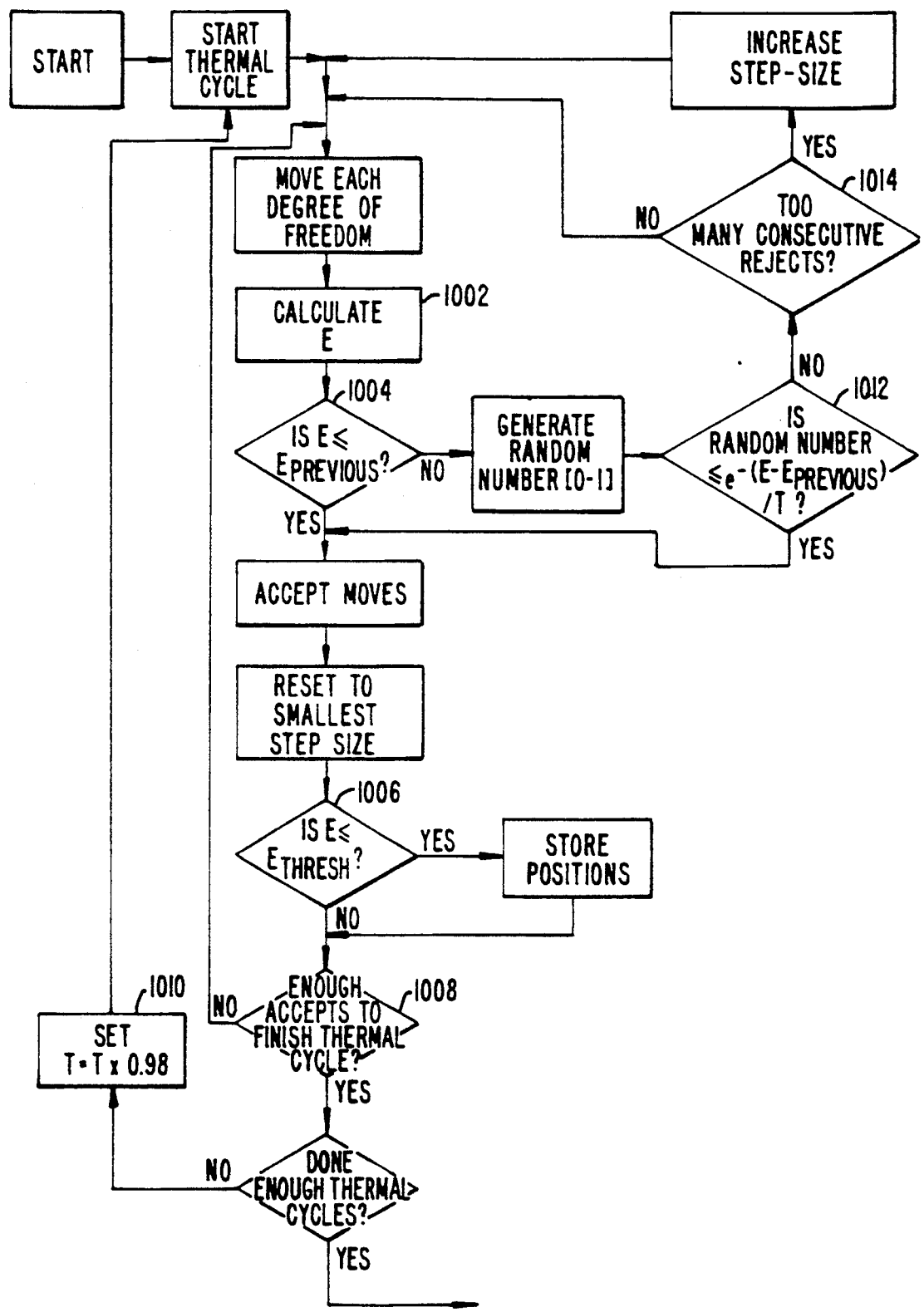
FIG. 6d schematically illustrates the main program for calculating the peptide packing conformation.
Figure 7A:
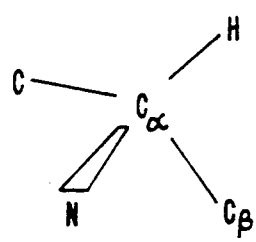
FIGS. 7a and 7b schematically show the bond between $C_\beta$ and the plane formed by C, $C_\alpha$ and N.
Figure 7B:
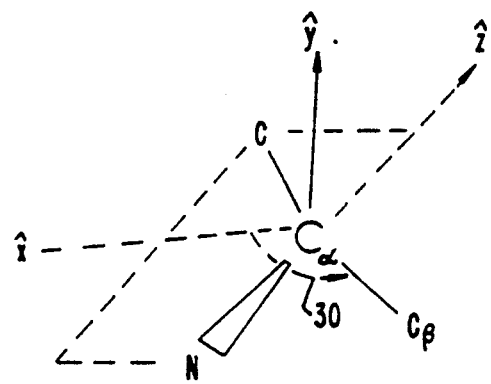
Figure 7C:
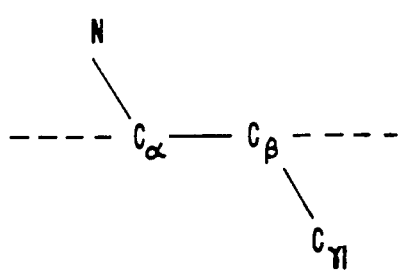
FIGS. 7c and 7d schematically illustrate the torsion angle about the bond between $C_\beta$ and $C_{60}$.
Figure 7D:
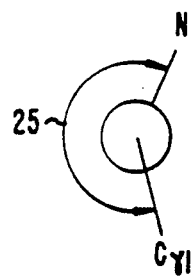

The main program is illustrated in FIG. 6d. Each thermal cycle is conducted at a new temperature (set at 1010). Within each thermal cycle, a number of moves are made to explore conformation space. After it is determined that a sufficient number of steps have been taken (step 1008), the thermal cycle is completed. After enough thermal cycles have been conducted, the run is finished. After each move within the thermal cycle, the energy of the new conformation is calculated and compared with the energy of the previous conformation (steps 1002 and 1004). If the energy of the new conformation is less than that of the previous conformation, the move is accepted and the new conformation energy is compared with a threshold energy (step 1006) and stored if it is below the threshold. At step 1004, if the energy of the new conformation is greater than that of the previous conformation, the probability of making the move is calculated and a decision to move is made based upon that probability (step 1013). If the move is rejected, the routine determines whether there have been too many consecutive rejects (step 1014). If so, the step size of each move is increased.

In a preferred embodiment, a group of computer programs written in c is used to perform set up and execution of the method of this invention. These routines were compiled and ran on a Silicon Graphics Iris 4D/240GTX computer. The main program employed to perform simulated annealing is known as "carbomb" (attached here to as Appendix B). At the conclusion of a run, "carbomb" provides the packing information for several low energy conformations of the test peptide at the final temperature of the run. These results are then used by another routine. ccarsick" (attached hereto as Appendix I), which p the information as described below. As described above, this information can be used to determine the packing or binding energy of the system being investigated. "carbomb" reads a binary input file produced by the routine "readpro" (attached hereto as Appendix C).

The information used by readpro to create the binary input file is taken from three files. First, a coordinate file is used to supply a list of the peptide atoms together with their Cartesian coordinates. One source of such lists is the Brookhaven Protein Data Bank (PDB). In addition, "plib" (attached hereto as Appendix A), which is described in detail above, provides, among other information, the types of atoms, each of the amino acids, their movement order and van der Waals constants. Plib and the PDB data are used by the routine "applib" (attached hereto as Appendix E) to create text describing the information contained in plib and the PDB. Collection of this information is coordinated by "upset," a routine contained in "auxfiles" (attached hereto as Appendix G). The output of applib is used by "makegen" (attached hereto as Appendix F) to convert the text information from applib into local frames of reference for each degree of freedom. This information together with the output of resmap.lib is used by readpro (described above) to produce the binary data file used by the main routine cara. "psizer (attached hereto as Appendix H) determines the size of the files being sent to readpro and allocates memory sufficient to store this information.

IX. Set-up and Precalculation

Referring to FIG. 6b, the set-up and precalculation steps are shown schematically in a flow chart. In step 300, the coordinates of the main chain atoms are used as input to determine the position of $C_\beta$ (step 302). Pairwise interaction tables are calculated (step 304), initial conformations are assigned to each side chain (step 306) and the steric energy is calculated for this initial conformation (step 308).

To use computer resources efficiently, a preferred embodiment of the invention uses look-up tables to tabulate pairwise interactions between atoms in the peptide. The first look-up table lists side chain-main chain atom interactions while the second table lists side chain-side chain interactions. These lists reflect the notion that atoms in separate three-dimensional areas of the peptide do not interact and, thus, should not be considered. Referring to FIG. 6c, construction of the first list begins by first classifying atoms as moving or stationary. Stationary atoms are not moved during the minimization and include all main chain atoms, as well as $C^\beta$ atoms, and any other atoms in the peptide (including any desired side chains) that are held fixed in space during the minimization. A pairwise list of which moving atoms that could interact with main chain atoms is generated by moving the side chains through representative conformations and tabulating the atoms of the moving side chain with atoms of the main chain. This pairwise interaction list is a boolean list that indicates which atoms could possibly interact with other moving atoms.

To calculate interactions between mobile side chain atoms more efficiently during the minimization process, a list of all pairwise interactions approaching close enough for significant van der Waals interaction was prepared before the energy minimization. To assess the closest approach distance for each pair of side chain atoms, each pair of side chain atoms was "aimed" at one another by twisting the appropriate torsions to minimize the distance between them. If the approach distance was less than 5 Å, the pair of atoms was added to the interaction list. During the minimization process, the total list of possible pairwise interactions was scanned periodically. Only the interaction energy for atom pairs less than 6 Å apart were calculated during the 10 subsequent steps, thus further reducing the number of interactions that had to be calculated to only those atomic interactions that made a significant energetic contribution. To ensure that the look-up tables were valid, the current interaction list was updated frequently enough to preserve the accuracy of the calculated energy.

To start the minimization in a preferred embodiment, all side-chain torsions are set to random angles selected in the range of 0° to 360° and having a uniform probability distribution. In other embodiments, the side chains are placed in predetermined positions according to, for example, the crystal structure data on homologous or mutant/wild type enzyme. A preferred starting temperature gives a move accept/reject ratio of 50%, that is, the temperature at which 50% of the proposed moves being accepted (referred to hereafter as $T_{50}$). At this temperature, the average energy and standard deviation of the energy are similar to that of the entire solution space, and the walk frequently attains energy levels signifying energy maxima. To find $T_{50}$ the minimization method initially adjusts its temperature rapidly until the accept/reject ratio fraction falls close to 50% and then begins annealing. As shown in FIG. 6d, the method gradually reduces the annealing temperature and the walk locates minima. The structures having the lowest energy are stored. When the fraction of accepts falls below 20%, the walk is terminated.

X. Post Processing

Energy minimization for typical peptides generates approximately 2000 conformations having energy lower than $3\sigma$ below the mean conformation energy. According to a preferred embodiment, a single predicted structure is synthesized from this aggregate set by calculating a weighted average energy for each residue in each of its possible conformations. The conformation with the lowest energy average over the set is taken as the predicted structure for the residue. The weighted average energy for a given conformation (specified by $\chi_1$ and $\chi_2$) is calculated according to the following expression:

$$E_{av}(\chi_1,\chi_2) = \Sigma E_i(\chi_1,\chi_2) \, e^{-E_i(\chi_1,\chi_2)/E_{wc}} / \Sigma e^{-E_i(\chi_1,\chi_2)/E_{wt}}$$

where $E_{wt}$ is the weighting energy determining how selective the average should be. This is simply a Boltzman average, treating the set of reported structures as a canonical ensemble. For side-chains with 3 or more torsions, the best position for the $\chi_1$ and $\chi_2$ torsions is determined via the weighted average; once all residues have been solved out to $\chi_2$ in this way, the remaining $\chi_3$ and $\chi_4$ torsions are solved simply by spinning them independently through their full range to find the lowest energy conformation for each residue.

XI. Selection of Residues for Prediction

The method is able to predict side chain conformations in local zones of 5 to 15 residues within a protein and also to simultaneously predict all the side chain conformations of whole proteins. In some cases, it may be advantageous to predict the conformations of only a fraction of all the side chains of the peptide. For example, some peptides will have conformations that are well known from x-ray crystallography or other techniques, but mutants of these peptides will have slightly perturbed structures. Because it can be expected that the mutant structure will deviate from the wild-type peptide structure only at certain localities, e.g. near the mutation site, the side chains that are sufficiently separated from these localities may, in certain circumstances, be held in fixed conformations during annealing. These fixed conformations preferably correspond to the known conformations of the wild-type peptide. The initial conformations of peptides in the vicinity of the mutation may be selected randomly or on the basis of some preferred pattern, such as the wild-type conformation. This approach may require considerably fewer computations when the overall peptide size is large in comparison to the mutated region(s).

For the results described in the Examples section, 9 proteins (crambin, 1crn; bovine pancreatic trypsin inhibitor, 5pti; the C-terminal domain of the ribosomal protein L7/L12, 1ctf; human lysozyme, 1lzl; ribonuclease A, 1rn3; 434cro, 2cro; flavodoxin, 4fxn; thermolysin, 3tln; and penicillopepsin, 2app) have been considered. The results of the method were compared with their high-resolution, accurate crystal structures. The 7 smaller structures fell well within the computer program's memory limitations for simultaneous prediction of all side chains possessing free $\chi$ torsions. For each of these peptides the method used the crystal structure coordinates for main chain and $C^{\beta}$ atoms, and all proline atoms, as the basis for the predictions, which were each generated in a single annealing run per protein. To keep the definition of side chain r.m.s. deviation consistent, the calculated side chain r.m.s. values included the $C^{\beta}$ atoms which were drawn directly from the native coordinate set. For side-chains having an axis of rotational symmetry (for example phenylalanine, tyrosine, aspartic acid, glutamic acid), the r.m.s. and torsion angle comparisons with the X-ray structure accounted for this symmetry by explicitly applying an appropriate symmetry operator (in this case a 2-fold rotation axis) to each such residue and selecting the conformation with the lower error.

For each of the 2 larger proteins (app, tln) the minimization method predicted only the conformations of approximately 100 of the most buried residues. The computer memory size was not large enough to handle and predict all the side chains in the protein. In both of these cases, the method only used main chain, $C^{\beta}$, and proline atoms for prediction; to avoid prejudicing the predictions, the coordinates for the remaining unpredicted surface side chains were wholly deleted prior to annealing. This deletion prevents the surface side chains, which would otherwise be locked into their correct conformations, from strongly biasing the predictions towards the native structure. In preferred embodiments, the method does not compensate for their absence, and the empty space left in the interior of the peptide by their disappearance does not appear to have weakened the prediction. To select the buried residues for prediction, a simple algorithm which calculates the fraction of accessible surface area for each residue (similar to the method of Connolly, J. Amer. Chem. Soc. (1985) Vol. 107, pg. 1118, which is incorporated herein by reference for all purposes) was employed with a simple cutoff value that allowed for including about one-third of the residues in each protein.

As described above, the prediction procedure is broken into 3 separate stages: setup, annealing and averaging. The setup program performs a variety of precalculations, generating parameter files needed to drive the annealing program. For prediction of all residues in flavodoxin (138 residues). Setup took 30 minutes running on 1 CPU of a Silicon Graphics Iris 40/240 GTX. The annealing program performs a single cooling cycle of simulated annealing and saves the low energy conformations it finds; for the same flavodoxin prediction this step required 8 CPU hours. Finally, the stored conformations are combined in a Boltzman-weighted average to produce the final prediction. This step took 2 min CPU time for flavodoxin.

XII. Chemical Synthesis of Mutated Peptides

Mutated peptides within the scope of the present invention can be synthesized chemically by means well-known in the art such as, Merrifield solid phase peptide synthesis and its modern variants. For an exhaustive overview of chemical peptide synthesis, see Principles of Peptide Synthesis, M. Bodansky, Springer, Verlag (1984); Solid Phase Peptide Synthesis, J. M. Stewart and J. B. Young, 2d ed., Pierce Chemical Co. (1984); The Peptides: Analysis, Synthesis, and Biology, (pp. 3–285) G. Barany and R. B. Merrifield, Academic Press (1980). Each of these references is hereby incorporated by reference for all purposes. In the solid-phase method, the synthesis starts at the carboxyl-terminal end of the peptide by attaching an alpha-amino protected amino acid such as, t-butyloxycarbonyl (Boc) or fluorenylmethyloxycarbonyl (Fmoc) protective groups, to a solid support. Suitable polystyrene resins consist of insoluble copolymers of styrene with about 0.5 to 2% of a cross-linking agent, such as divinyl benzene. These and other methods of peptide synthesis are also exemplified by U.S. Pat. Nos. 3,862,925, 3,842,067, 3,972,859, and 4,105,602.

The synthesis uses manual synthesis techniques, as in traditional Merrifield synthesis, or automatically employs peptide synthesizers. Both manual and automatic techniques are well known in the art of peptide chemistry. The resulting peptides can be cleaved from the support resins using standard techniques, such as HF (hydrofluoric acid) deprotection protocols as described in Lu, G.S., Int. J. Peptide & Protein Res (1987) vol 29, pg. 545. Other cleavage methods include the use of hydrazine or TFA (tri-fluoracetic acid).

XIII. Recombinant Production of Mutated Peptides

As an alternative to chemical synthesis, the mutated peptide designed by the methods described in the present disclosure can be produced by expression of recombinant DNA constructs prepared according to well-known methods. Such production can be desirable when large quantities are needed or when many different mutated peptides are required. Since the DNA of the wild-type (or other related) peptide has often been isolated, mutation into modified peptide is possible.

The DNA encoding the mutated peptides is preferably prepared using commercially available nucleic acid synthesis methods. See Gait et al. "Oligonucleotide Synthesis; A Practical Approach" M. J. Gait, Ed., IRL Press, Oxford, England (1985) for a current overview of nucleic acid synthesis methods. Methods to construct expression systems for production in either natural or recombinant hosts are generally known in the art.

Expression can be affected in either procaryotic or eucaryotic hosts. Procaryotes most frequently are represented by various strains of E. Coli. However, other microbial strains may also be used, such as bacilli, for example Bacillus subtilis, species of pseudomonas, or other bacterial strains. In such procaryotic hosts, plasmid vectors that contain replication sites and control sequences derived from a species compatible with the host are used. For example, a common vector for E. coli is pBR322 and its derivatives. Commonly used procaryotic control sequences, which contain promoters for transcription initiation, optionally with an operator, along with ribosome binding-site sequences, include such commonly used promoters as the beta-lactamase and lactose (lac) promoter systems, the tryptophan (trp) promoter system, and the lambda-derived $P_L$ promoter. However, any available promoter system compatible with procaryotes can be used.

Expression systems useful in eucaryotic hosts consist of promoters derived from appropriate eucaryotic genes. A class of promoters useful in yeast, for example, includes promoters for synthesis of glycolytic enzymes, such as 3-phosphoglycerate kinase. Other yeast promoters include those from the enolase gene or the Leu2 gene obtained from YEp13.

Suitable mammalian promoters include the early and late promoters from SV40 or other viral promoters such as those derived from polyoma, adenovirus II, bovine papilloma virus or avian sarcoma viruses. Suitable viral and mammalian enhancers are cited above. When plant cells are used as an expression system, the nopaline synthesis promoter, for example, is appropriate.

The expression systems are constructed using well-known restriction and ligation techniques and transformed into appropriate hosts. Transformation is done using standard techniques appropriate to such cells. The cells containing the expression systems are cultured under conditions appropriate for production.

It will be readily appreciated by those having ordinary skill in the art of peptide design that the mutated peptides that are designed in accordance with the present disclosure and subsequently synthesized are themselves novel and useful compounds and are thus within the scope of the invention.

XIV. Physical Stability Assay

After the mutated peptides have been synthesized by either chemical or recombinant methods, the physical stabilities can be measured using a variety of physical techniques.

For example, thermal stability can be determined by assaying a specific property of the mutated protein at different temperatures as is well known in the art. Physical stability is a structural property, and generally indicates the stability of a folded conformation of the peptide relative to an unfolded or denatured state. Many methods such as spectroscopy, sedimentation analysis, chemical assays, etc. can determine whether a peptide has undergone a structure change. For example, NMR, circular dichroism, fluorescent transfer, etc. can measure the folded state of a peptide at different conditions.

XV. EXAMPLES

The following examples are meant to exemplify the methods described herein rather than limit their scope.

To test the invention's accuracy for residues that are both exposed to the solvent and buried in the interior, the method was used to predict side-chain conformations for a set of nine proteins ranging in size from 45 to 323 residues. In seven of these cases, all side-chains possessing $\chi$ torsions were moved and predicted simultaneously; for the largest two proteins (app and tln) only the most buried residues (roughly ⅓ of the residues in each protein) were included in the predictions. Table 2 presents the r.m.s. deviations (in Å) of the predicted side chain atoms, relative to the X-ray structure.

TABLE 2

| PEPTIDE | OVERALL | CORE RESIDUES |
|---|---|---|
| crn | 1.65 | 1.23 |
| pti | 2.61 | 1.65 |
| ctr | 1.86 | 1.15 |
| cro | 2.39 | 1.15 |
| rns | 1.86 | 1.24 |
| lz | 1.62 | 1.08 |
| fxn | 1.90 | 1.53 |
| tln | 1.28 | 1.53 |

TABLE 2-continued

| PEPTIDE | OVERALL | CORE RESIDUES |
|---|---|---|
| app | 1.12 | 1.53 |
| All peptides | 1.77 | |
| Whole peptides only | 1.97 | |
| Core residues only | | 1.25 |

Whole peptides refer to the seven peptides where the invention method simultaneously predicted all side chain free torsions. In the app and tln peptides, the method predicted only the residues most buried in the peptide's interior.

The predictions ranged in accuracy from 2.61 Å r.m.s. to 1.12 Å (best), with an overall r.m.s. error of 1.77 Å for the prediction set. The method worked better for residues buried in the interior of the peptide than those exposed to solvent, predicting the core residues of app and tln peptides with r.m.s. values of 1.12 Å and 1.28 Å, respectively. The overall r.m.s. error for core residues was 1.25 Å for the entire set (Preley et al. *Tech. Prot. Chem. II* (1991) pg 115; and Boyd et al. *Tetrahedron Letters* (1990) vol. 27, pg. 3849; which are all incorporated by reference for all purposes).

The residue prediction r.m.s. errors in the worst cases (pti and cro) were due primarily to a small fraction of the total residues predicted. For pti (overall side chain r.m.s.=2.61 Å), 71% of the residues had r.m.s. values <2 Å, while 76% of the $\chi_1$ predictions and 55% of the $\chi_2$ predictions were within 40° of correct. Similarly, in cro peptide (r.m.s. =2.39 Å) these fractions were 77%, 89% and 69%, respectively. The errors contributing to the high r.m.s. values of these protein were systematically concentrated in a few types of residues, and were mostly at the peptide surface. In the pti peptide, arginine (having an individual r.m.s. error of 4.51 Å for n=6 cases), lysine (r.m.s.=2.71 Å, n=4) and glutamate (r.m.s.=2.60 Å, n=2) were the only residue types with r.m.s. values as large or larger than the overall value (2.61 Å), and were all located at the protein surface. Surface residues constituted the bulk of the remaining errors as well. The unusually high 2.17 Å r.m.s. for phenylalanine in the pti peptide (compared with 1.25 Å in the overall set) was due to a single surface phenylalanine which the minimization algorithm rotated out into solvent in an effort to relieve van der Waals collisions. The prediction for this exposed residue had an r.m.s. error of 4.20 Å, while the other three phenylalanine residues in the protein were between 0.48 Å and 0.71 Å r.m.s. A similar error was made for a single surface tyrosine (r.m.s. =3.43 Å, versus 0.19 Å to 0.94 Å r.m.s. for the other 3 tyrosine residues in the pti peptide). The only other residue type in pti with r.m.s. values greater than 1.5 Å was aspartate (r.m.s.=1.81 Å, n=3). Again, all these aspartates were on the peptide surface and exposed to solvent.

The errors responsible for the high overall r.m.s. value of cro (2.43 Å) followed the same pattern. Arginine (4.43 Å, n=5), phenylalanine (3.35 Å, n=2), and lysine (2.87 Å, n=6) were the only residue types with r.m.s. values at or above the overall value, and in all these cases the errors were for surface residues largely unconstrained by packing. Of the two phenylalanine residues in the cro peptide, the one at the peptide surface was predicted to be rotated into solvent (r.m.s.=4.65 Å), while the one in the core was correct (r.m.s.=0.92 Å). The remaining residue types with r.m.s. values above 1.5 Å were glutamine (2.20 Å, n=6), tryptophan (2.10 Å, n=1) and asparagine (1.61 Å, n=1); all were exposed at the peptide surface.

Thus, exposed residues posed some problems for the particular prediction method described above. This may be because electrostatic interactions which were not included were frequently important for determining conformations of the exposed residues. In addition, the described program had no energy function representing the hydrophobic effect and, as a result, often mispredicted residues by failing to bury them appropriately. This was the case for the tryptophan in the cro peptide, which in the native structure lies flat in a shallow groove on the surface. The method predicted it in the correct orientation, but erroneously raised it slightly from the groove.

In other embodiments of the invention, additional energy terms are added to the potential energy function. Suitable terms can account for electrostatic attraction/repulsion, hydrophobic packing, entropic ordering of solvent.

The clustering of errors in a small subset of surface residues prevailed over the entire set of predicted peptides. In the whole-peptide predictions, the fraction of residues predicted within 2 Å r.m.s. ranged from 71 to 81%, while the fraction of $\chi_1$ angles within 40 degrees varied from 57 to 89% (50 to 69% for $\chi_2$). Once again, these ratios were markedly better in the buried-core predictions (app and tln): 91 to 92%, 81 to 82% and 74 to 81%, respectively, for r.m.s. $\chi_1$ and $\chi_2$. Lysine, arginine and glutamate were frequently the only residue types with errors larger than the overall value in each protein.

To quantify prediction accuracy for each residue type, a "quality factor" for each residue type was calculated by dividing the expected r.m.s. error for a random conformation by the actual error of the predictions. The quality factor thus indicates the ratio of movement of the predictions' r.m.s. error over random error. The method predicted large hydrophobic side-chains, especially tyrosine, phenylalanine, methionine, leucine and isoleucine, best. Charged residues, particularly lysine and arginine, and very small residues such as serine, threonine and cysteine had the lowest quality ratios. Poor prediction of serine and threonine residues resulted both from their small size (which gives them reduced steric hindrance) and the importance of hydrogen bonds for determining their conformation. Cysteine residues had a high error rate because the algorithm made no effort to identify potential disulfide bridges, and effectively prohibited their formation by using the normal sulfur van der Waals radius for cysteine-cysteine interactions, which gives an energy minimum at an interatomic separation of 4.3 Å. Where disulfides did occur in native structures, the prediction typically placed one cysteine of the pair in the correct location, forcing the other into a rotamer 120° away from the correct position. Finally, comparison of a residues' quality factor against side-chain volume reveals a loose correlation between prediction accuracy and the residues' size, especially for hydrophobic side-chains; charged and polar residues uniformly fell below this correlation.

To assess reliability and consistency, the invention method generated seven separate predictions for one protein (4fxn), each starting from different random conformations. All converged well and the method gave a consistent prediction that was independent of peptide starting conformation. Each of these predictions had overall predicted side chain r.m.s. errors from the native structure between 1.59 to 1.90 Å, versus the random starting conformations' side-chain r.m.s. value of 3.00 to 3.34 Å. The r.m.s. error for buried residues in the different predictions ranged from 1.15 to 1.55 Å, with very little deviation (0.2 to 0.8 Å) in the predictions of hydrophobic side-chains such as phenylalanine, tyrosine, isoleucine, leucine and valine. In contrast, charged residues had internal r.m.s. deviations around 2 Å.

Starting from the observation that poorly predicted residue types had high internal r.m.s. deviations, it was found that the internal r.m.s. deviation for each residue over the set of predictions was a strong predictor of the accuracy of its predicted conformations against the native crystal structure. In general, a residue's r.m.s. from the native crystal structure was never significantly less than its internal r.m.s. deviation over the set of predictions from different random starts. This observation provides a useful internal indication of probable errors that offers ways to obtain improved predictions. In general, the idea of using multiple predictions for detecting errors and improving accuracy should be a powerful tool for modelling.

The invention method clearly demonstrates that packing constraints determine the side chain conformations of different residue types. Hydrophobic side chains inside proteins, especially large residues such as phenylalanine and tyrosine, are generally constrained to unique conformations by packing forces. When located at the protein surface, however, such side chains often have alternative conformations which in actual protein folds are ruled out by the hydrophobic effect. Small polar side-chains, such as serine and threonine, are typically constrained to one or two possible conformations, with hydrogen bonding selecting the appropriate one. Surface residues are poorly constrained by packing.

The invention method also underscores the importance of packing for determining the internal structure of peptides. The observation that van der Waals interactions alone are sufficient to predict the internal structure of proteins accurately and comprehensively suggests that there may not be significant alternative ways of packing a given sequence of side-chains into the internal architecture established by the main-chain fold. The convergence of the multiple flavodoxin predictions, from completely different starting points, to a single predicted core structure demonstrates that the invention method successfully explores the full conformational space. This result is consistent with experimental and theoretical work indicating the importance of packing in determining core structure. Specifically, it suggests that packing constraints enforce a one-to-one correspondence between the main-chain fold and the pattern of side-chain packing that constitutes the protein core.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

---

What is claimed is:

1. A method for determining the three dimensional structure of a peptide, the peptide having amino acid side chains extending from a defined main chain backbone, each amino acid side chain having predefined rotational degrees of freedom, the method comprising the steps of:
  a. inputting coordinates of the main chain backbone of said peptide;
  b. constructing an initial three dimensional peptide conformation by placing the amino acid side chains on said main chain backbone coordinates, the peptide being in an initial three dimensional peptide conformation;
  c. randomly rotating said amino acid side chains around said predefined rotational degrees of freedom by small rotational perturbations to produce a modified three dimensional peptide conformation;
  d. determining the side chain steric interaction energy for said modified peptide conformation;
  e. creating a final three dimensional peptide conformation by reducing said side chain steric interaction energy by repeating steps c-d, wherein said step of randomly rotating is biased toward conformations having lower values of said side chain steric interaction energy and wherein said interaction energy is truncated if it exceeds a preselected maximum.

2. A method according to claim 1 wherein step e is conducted with simulated annealing.

3. A method according to claim 2 further comprising the steps of:
  e. creating additional final three dimensional peptide conformations by conducting steps b-e repeatedly; and
  f. averaging said final three dimensional peptide conformations to produce an average three dimensional peptide conformation.

4. A method according to claim 2 wherein the step of reducing said side chain steric interaction energy comprises minimizing said side chain steric interaction energy of the peptide.

5. A method according to claim 3 wherein the step of averaging said three dimensional peptide conformations comprises the step of selecting an energetically stable side chain conformation for each side chain of the peptide, wherein each said energetically stable side chain conformation is selected from the group consisting of corresponding side chain conformations from said three dimensional models.

6. A method according to claim 5 wherein each selected energetically stable side chain conformation has the lowest steric interaction energy.

7. A method according to claim 1 wherein the defined main chain backbone of said peptide comprises $C_i^a$, $N_i$, $I_i$, and $C_i$ of each said amino acid.

8. A method according to claim 1 wherein the step of constructing an initial three-dimensional peptide conformation comprises:
  a. determining the three dimensional position of $C_i^a$ for each amino acid side chain; and
  b. assigning a torsion angle to each predefined rotational degree of freedom.

9. A method according to claim 8 wherein each said torsion angle is selected randomly.

10. A method according to claim 8 wherein a plurality of torsion angles are selected randomly and a plurality of torsion angles are predefined.

11. A method according to claim 1 wherein said steric interaction energy is calculated according to the Lennard-Jones potential:

$$E_{VDW} = \epsilon_0 \left[ \left( \frac{r_0}{r} \right)^{12} - 2 \left( \frac{r_0}{r} \right)^6 \right]$$

wherein r is the interatomic distance;
  $r_0$ is the equilibrium interatomic distance; and
  $\epsilon_0$ is the depth of energy well for the interaction.

12. A method according to claim 11 wherein the Lennard-Jones potential is truncated to a predetermined maximum energy in the range of about 4 to 15 kcal/mol.

13. A method according to claim 1 further comprising a step of determining torsional interaction energies between adjacent carbon atoms.

14. A method according to claim 13 wherein said torsional interaction energy is calculated according to the equation:

$$E_{torsion} = K \cos[n(\chi - d)]$$

wherein K is an empirical energy constant, n and d are constants and $\chi$ is a torsion angle between adjacent carbon atoms.

15. A method according to claim 14 where K is between about 1 and about 5 Kcal/mol, and wherein n is 3 and d is 0.

16. A method according to claim 1 wherein each amino acid side chain rotational degree of freedom is rotated by an angle randomly selected in the range between $-25°$ and $25°$.

17. A method according to claim 16 wherein each amino acid side chain rotational degree of freedom is rotated by an angle randomly selected in the range between $-12°$ and $12°$.

18. A method according to claim 1 wherein each amino acid side chain rotational degree of freedom is rotated by an angle randomly selected from the group consisting of approximately $-10°$, approximately $0°$, and approximately $10°$.

19. The method according to claim 1 wherein the step of randomly rotating is biased toward conformations having lower values of said side chain steric interaction energy by selectively accepting said modified three dimensional peptide conformations, the step of selectively accepting comprising:
comparing the steric interaction energy of a current modified peptide conformation with the interaction energy of a previous peptide conformation; and
reverting to said previous peptide conformation according to a predetermined probability when the interaction energy of said modified peptide conformation is higher than the interaction energy of said previous peptide conformation.

20. A method according to claim 19 wherein said predetermined probability is represented by:

$$P = \exp(-E_{diff}/kT),$$

wherein $E_{diff}$ is the steric interaction energy difference between the modified peptide conformation and the previous peptide conformation, k is the boltzman constant, and T is a predetermined constant.

21. A method for determining the three dimensional structure of a peptide, the peptide having a plurality of amino acid side chains extending from a defined main chain backbone, each amino acid side chain having predefined rotational degrees of freedom, and the plurality of side chains having a plurality of conformations defining a conformation space, the method comprising the steps of:
a. constructing an initial three dimensional peptide conformation by placing each amino acid side chain in an initial three dimensional conformation;
b. determining a side chain steric interaction energy for said initial peptide conformation; and
c. searching the full conformation space for low energy peptide conformations by randomly rotating each of said plurality of amino acid side chains around respective predefined rotational degrees of freedom to produce a modified three dimensional peptide conformation and determining side chain steric interaction energy for said modified peptide conformation, said low energy peptide conformations representing the three dimensional structure of said peptide.

22. A method of producing a three-dimensional image of a peptide with the aid of a digital computer, the peptide having a primary sequence, main chain coordinates, and side chains bonded to the main chain, the side chains comprising atoms connected to one another and the main chain by side chain bonds, the method comprising the following steps:
storing the primary sequence, the main chain coordinates, and the side chains in a computer useable form;
repeatedly moving selected side chain atoms by rotation about selected side chain bonds to conformations having a low steric interaction potential, the rotation distance and direction determined by simulated annealing;
producing a final three dimensional conformation of the peptide by conducting simulated annealing for a predetermined length; and
displaying an image of the final three dimensional conformation on a display monitor.

23. The method recited in claim 22 further comprising a step of storing conformations having steric interaction potentials below a predefined value.

24. The method recited in claim 22 wherein the steric interaction potential is determined according to the Lennard-Jones potential, and wherein the value of the Lennard-Jones potential is truncated when it exceeds a predetermined value.

25. A system for determining the three-dimensional conformation of a peptide, the peptide having a primary sequence, main chain coordinates, and side chains bonded to the main chain, the side chains comprising atoms connected to one another and the main chain by side chain bonds, the system comprising:
means for converting the primary sequence and main chain coordinates of the peptide to a computer useable form;
means for bonding the side chains to the main chain in a random orientation to form an initial peptide conformation;
means for rotating selected side chain atoms about selected side chain bonds to form intermediate peptide conformations;
means for determining the steric interaction energy of the intermediate peptide conformations;
means for condensing the intermediate peptide conformations to produce a final peptide conformation by simulated annealing; and
means for displaying images of the final peptide conformation.

26. The system of claim 25 wherein means for displaying images is a computer display terminal.

* * * * *

UNITED STATES PATENT AND TRADEMARK OFFICE
CERTIFICATE OF CORRECTION

PATENT NO. : 5,241,470
DATED : August 31, 1993
INVENTOR(S) : Christopher Lee and Subramanian Subbiah It is certified that error appears in the above-indentified patent and that said Letters Patent is hereby corrected as shown below:

At column 1, line 4, please insert the following:

--This invention was made with government support under grant number GM-41455 awarded by the National Institutes of Health. The government has certain rights in the invention.--

Signed and Sealed this

Twenty-fifth Day of October, 1994

Attest:

BRUCE LEHMAN

*Attesting Officer*  *Commissioner of Patents and Trademarks*